United States Patent

Speronello

[11] Patent Number: 5,974,810
[45] Date of Patent: Nov. 2, 1999

[54] METHOD AND COMPOSITION FOR PREVENTING ODORS IN ICE

[75] Inventor: Barry K. Speronello, Belle Mead, N.J.

[73] Assignee: Engelhard Corporation, Iselin, N.J.

[21] Appl. No.: 08/961,488

[22] Filed: Oct. 30, 1997

Related U.S. Application Data

[63] Continuation-in-part of application No. 08/891,665, Jul. 11, 1997, abandoned, which is a continuation-in-part of application No. 08/808,768, Mar. 3, 1997, abandoned.

[51] Int. Cl.⁶ ....................................................... F25C 1/00
[52] U.S. Cl. .................................................... 62/66; 62/69
[58] Field of Search ............................................. 62/66, 69

[56] References Cited

U.S. PATENT DOCUMENTS

| 4,832,972 | 5/1989 | Toledo-Flores et al. ................ 426/327 |
| 5,476,579 | 12/1995 | Choi et al. ................................. 204/95 |

*Primary Examiner*—William E. Tapolcai
*Attorney, Agent, or Firm*—Stephen I. Miller

[57] ABSTRACT

A method for producing ice having substantially no undesirable taste and odor characteristics is disclosed.

9 Claims, 3 Drawing Sheets

METHOD AND COMPOSITION FOR PREVENTING ODORS IN ICE

RELATED APPLICATION

This is a Continuation-In-Part Application of U.S. Ser. No. 08/891,665 filed Jul. 11, 1997, now abandoned, which itself is a Continuation-In-Part Application of U.S. Ser. No. 08/808,768 filed Mar. 3, 1997, now abandoned.

FIELD OF THE INVENTION

The present invention is generally directed to the controlled release of chlorine dioxide gas from the reaction of a metal chlorite and a second material which reacts with the metal chlorite in the presence of water vapor but will not react with the metal chlorite in the substantial absence of liquid water or water vapor. Once the reaction commences, chlorine dioxide gas is produced in a sustained concentration of about 0.025 to 1,000 ppm.

BACKGROUND OF THE INVENTION

Gaseous chlorine dioxide in low concentrations (i.e. up to 1,000 ppm) has long been recognized as useful for the treatment of odors and microbes. Its use is particularly advantageous where microbes and/or organic odorants are sought to be controlled on and around foodstuffs, as chlorine dioxide functions without the formation of undesirable side products such as chloramines or chlorinated organic compounds that can be produced when elemental chlorine is utilized for the same or similar purposes. For example, if a low concentration of chlorine dioxide gas can be maintained in contact with fresh produce for several days during shipping from the farm to the local retailer, the rate of spoilage of the produce can be decreased. In addition, chlorine dioxide gas is also generally considered to be safe for human contact at the low concentrations that are effective for deodorization and most antimicrobial applications.

Chlorine dioxide gas can be toxic to humans at concentrations greater than 1,000 ppm and it can be explosive at concentrations above about 0.1 atmosphere. Therefore, chlorine dioxide gas is not manufactured and shipped under pressure like other industrial gases, and conventional methods of on-site manufacture require not only expensive generation equipment but also high levels of operator skill to avoid generating dangerously high concentrations. These problems have substantially limited the use of chlorine dioxide to large commercial applications, such as water treatment and poultry processing, where the consumption of chlorine dioxide is sufficiently large that it can justify the capital and operating costs of expensive equipment and skilled operators for on-site manufacture.

Commercially, chlorine dioxide is produced from a variety of aqueous solutions of chlorine-containing salts, for example see U.S. Pat. No. 5,009,875.

Attempts have also been made to produce chlorine dioxide using mixtures of solid reagents. Generally, the prior art has focused on three systems for chlorine dioxide production using solid reagents. One system employs a solid mixture of a metal chlorite and an acid in a liquid, aqueous environment. A second system combines a metal chlorite and an acid where chlorine dioxide gas is released under dry conditions. A third system employs the combination of a metal chlorite and a solid organic acid anhydride to generate a highly concentrated flow of chlorine dioxide which must be diluted with a constantly flowing stream of inert gas.

Each of these solid reagent systems is disadvantageous for any one or more of the following reasons:

a) upon mixing there is normally a sudden, highly concentrated stream of chlorine dioxide generated;

b) the mixture of reactants produces chlorine dioxide gas under dry conditions thereby reducing the shelf life of the reactants; and c) an inert gas stream must be used to reduce the concentration of chlorine dioxide gas in the atmosphere.

For example: U.S. Pat. No. 2,022,262 discloses the use of chlorine dioxide in aqueous solution in a stain removing process wherein the chlorine dioxide is produced upon acidification of an aqueous solution of alkali metal or alkaline earth metal chlorite salts (i.e. chlorites) with oxalic acid.

U.S. Pat. No. 2,071,091 discloses that chlorous acid which is produced upon acidification of solutions of alkali metal and alkaline earth metal chlorite salts is an effective fungicide and bactericide. This patent discloses solid compositions of metal chlorites and solid acids that will produce chlorine dioxide when dissolved in water. However, the materials of the '091 patent are useful only in "wet" applications where liquid water is available and where contacting a material to be treated with chlorine dioxide dissolved in liquid water is acceptable.

U.S. Pat. No. 2,071,094 discloses deodorizing compositions in the form of dry briquettes comprising a dry mixture of a soluble chlorite, an acidifying agent, and a filler of a lower solubility so that disintegration of a briquette is inhibited in the presence of liquid water. Generation of chlorine dioxide begins as the briquette dissolves in water. Such materials are subject to the same use limitations as those of the '091 Patent.

U.S. Pat. No. 2,482,891 discloses a material comprising a solid organic acid anhydride and an alkali metal or alkaline earth metal chlorite salt which is stabilized by the addition of a desiccant material. The combined solid material is described as evolving chlorine dioxide on contact with water. Example 1 describes the production of chlorine dioxide by contacting a mixture of sodium chlorite, phthalic anhydride and sodium monoxide with water vapor. It is not clear from the example whether or not the solid mixture was already in contact with liquid water. The resultant exit gas in this example contains a high concentration of chlorine dioxide gas. Also, the organic acid anhydride is potentially explosive in combination with the chlorite salt, as well as being a relatively expensive constituent. Therefore, this material has not been commercially successful.

U.S. Pat. No. 3,591,515 discloses solid pulverulent compositions comprising solid carriers having impregnated thereon stabilized solutions of chlorine dioxide or chlorites. When the solution-impregnated compositions are contacted with solid acids they release chlorine dioxide gas. Such materials are sold commercially today under the trade names OSTOBON® and ABSCENT® (by International Dioxide Inc., Clark, N.J.), but their commercial acceptance has been limited because they either prematurely release small amounts of chloride dioxide through the packaging on store shelves, or they require relatively complicated mixing of two ingredients by the user at the point of application.

U.S. Pat. No. 4,585,482 discloses a long-acting biocidal composition comprising a chlorite and an organic acid such that the pH of the composition is <7. Such compositions release chlorine dioxide in the presence of liquid water. This patent also discloses methods for producing dry microcapsules of such compositions with water having polymer shells such that the resultant dry materials release chlorine dioxide.

U.S. Pat. No. 4,547,381 discloses dry compositions for the sustained controlled release of gaseous chlorine dioxide comprising a dry inert diluent, a chlorite salt, and a dry agent capable of reacting with a chlorite in a dry state to produce chlorine dioxide gas. Such materials have not achieved substantial commercial success because they begin to release chlorine dioxide gas immediately upon formulation and, therefore, they must be mixed and utilized over a short time period.

U.S. Pat. No. 5,360,609 discloses the incorporation of a chlorine dioxide generating compound into a polymer or oligomer film which is then coated onto a substrate. The chlorite constituent is dissolved in a hydrogen bonded phase containing a monomeric or polymeric amide or alcohol. The hydrogen bonded phase is then mixed with an incompatible apolar phase containing an acid anhydride. Chlorine dioxide gas is released by direct reaction of the acid anhydride with the chlorite anion across the phase boundary. However, the process described in the '609 Patent employs relatively expensive materials and the reaction is potentially explosive due to the proximity of the strongly oxidizing metal chlorite with the carbonaceous polymers.

U.S. Pat. No. 5,567,405 discloses the generation of chlorine dioxide gas from mixed beds of zeolite crystals, where the first bed comprises a zeolite that has been impregnated with an aqueous solution of sodium chlorite and the second bed comprises a zeolite that has been impregnated with phosphoric, citric, or acetic acid. Chlorine dioxide gas is released when acid migrates from the second bed and contacts chlorite on the first bed. The first and second beds may be physically mixed together. The process disclosed in the '405 Patent requires expensive equipment and results in a product having a relatively short shelf-life.

It would therefore be a significant advance in the art of generating chlorine dioxide gas for commercial applications to have a method, composition and system in which the chlorine dioxide gas is generated under controlled conditions at low concentrations. It would be a further advance in the art to provide a method, composition and system in which the reactants do not generate chlorine dioxide gas in the absence of water but do provide a controlled sustained release of chlorine dioxide gas in the presence of water vapor. As a result, the composition of the present invention can be prepared in advance and stored under dry conditions without the premature release of chlorine dioxide gas. In this manner the need for skilled personnel to prepare the mixture on-site is avoided and shelf-life is enhanced.

SUMMARY OF THE INVENTION

The present invention is generally directed to a method, composition and system useful for the controlled release of chlorine dioxide gas at low concentrations when in the presence of water vapor. The reactants generating the chlorine dioxide gas when combined to form the composition do not generate a significant amount of chlorine dioxide gas when water vapor is not present. The reactants can therefore be stored for long periods of time in a substantially dry atmosphere.

In particular, the present invention is directed, in part, to a method of generating chlorine dioxide gas in a controlled release manner comprising:

a) forming a mixture of at least one metal chlorite and at least one second material, a dry solid hydrophilic material capable of reacting with the metal chlorite to produce chlorine dioxide gas in the presence of water vapor but not in the substantial absence of liquid water or water vapor (hereinafter "Second Material"); and b) exposing said mixture to an atmosphere comprising water vapor to produce chlorine dioxide gas in a sustained concentration of from about 0.025 to 1,000 ppm.

The present invention is also directed to compositions for the generation of chlorine dioxide gas in the form of a mixture of reactants. The reactants can be chosen to control both the rate and the duration of generation of chlorine dioxide gas.

BRIEF DESCRIPTION OF THE DRAWINGS

The following drawings are illustrative of embodiments of the invention and are not intended to limit the invention as encompassed by the claims forming part of the Application.

DETAILED DESCRIPTION OF THE INVENTION

Figure 1:
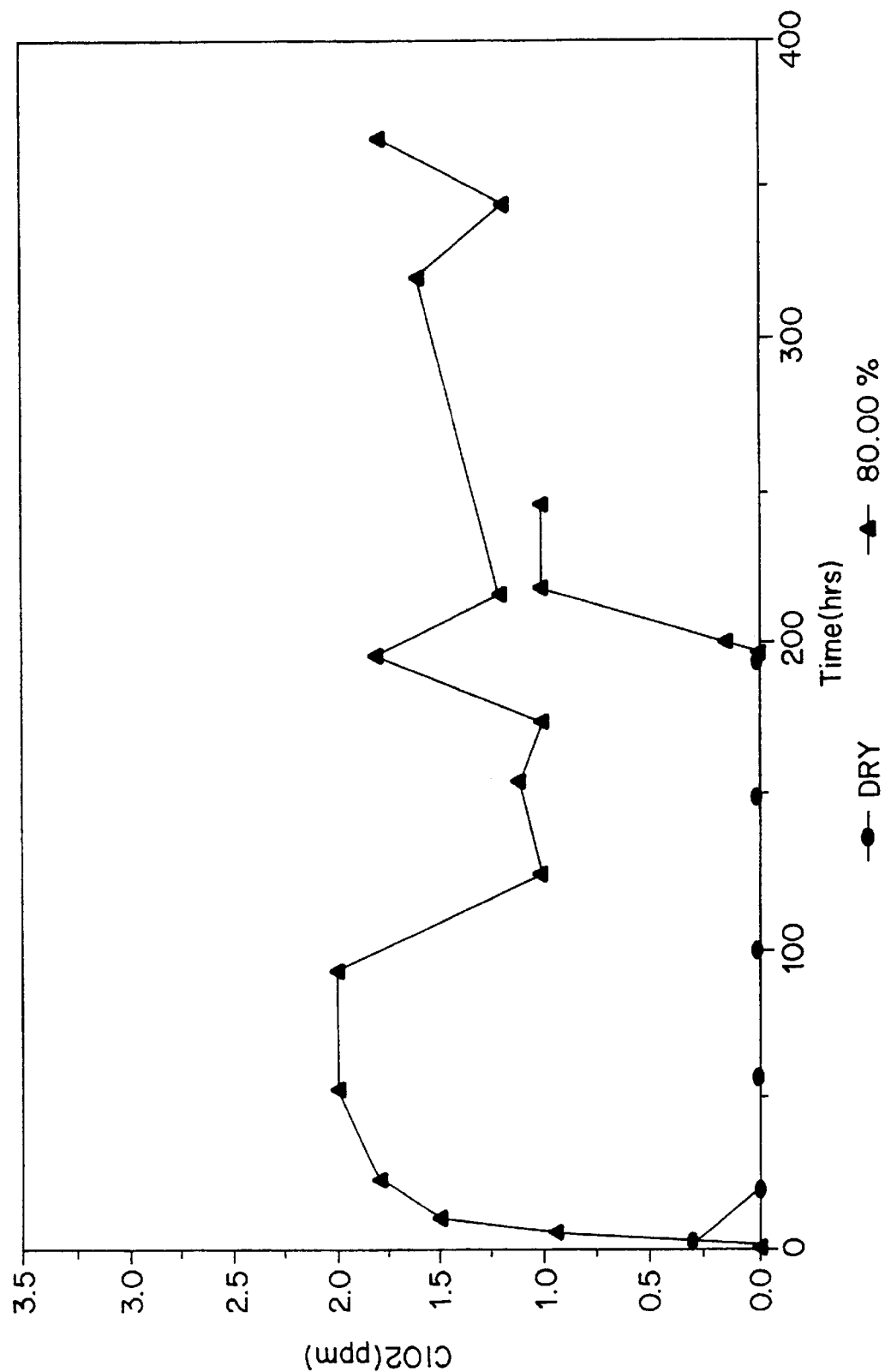
FIG. 1 is a graph showing the production of chlorine dioxide gas under dry and humid conditions for the first mixture prepared in accordance with Example 1.

The present invention is directed to a method, composition and system of generating chlorine dioxide gas in a controlled release manner. As used herein the phrase "controlled release manner" shall mean that the reactants comprising the composition produce chlorine dioxide gas at a rate of production which results in low concentrations of the gas as compared with prior art systems in which the generation of chlorine dioxide gas is made at high concentrations in a sudden and possibly explosive manner. In accordance with another aspect of the present invention, solid compositions for producing chlorine dioxide gas are provided in which the rate and duration of chlorine dioxide gas generation can be controlled.

The first step of the method is the formation of a composition in the form of a mixture of at least one metal chlorite and at least one Second Material. The metal chlorites employed in the present invention can generally be any metal chlorite. Preferred metal chlorites are alkali metal chlorites, such as sodium chlorite and potassium chlorite. Alkaline earth metal chlorites can also be employed. Examples of alkaline earth metal chlorites include barium chlorite, calcium chlorite, and magnesium chlorite. The most preferred metal chlorite is sodium chlorite.

The Second Material is a dry solid hydrophilic material, preferably a dry solid inorganic hydrophilic material. The preferred dry solid hydrophilic material produces a pH of no more than about 10.5 when the aqueous portion of a 30 weight percent mixture of that material in deionized water is measured. More preferred solid hydrophilic materials produce a pH of less than 9 and most preferably less than 7. Examples of such dry solid hydrophilic materials suitable for reacting with the metal chlorites include, but are not limited to, synthetic zeolites, such as A, X, Y, and mordenite; natural zeolites such as chabazite and clinoptilolite; hydrous clays, such as bentonite, kaolin, attapulgite and halloysite; calcined clays, such as metakaolin, spinel phase kaolin, calcined bentonite, calcined halloysite, and calcined attapulgite; acidified synthetic zeolites, such as A, X, Y, and mordenite that have been contacted with one or more acidic solutions containing sulfuric acid, hydrochloric acid, nitric acid, or other acidic compound (e.g. calcium chloride) so that the pH of the resulting aqueous phase of the mixture is below 10.5; acidified natural zeolites such as chabazite and clinoptilolite; acidified clays, such as bentonite, kaolin, attapulgite and halloysite that have been contacted with one or more acidic solutions containing sulfuric acid, hydrochloric acid, nitric acid, or other acidic compounds (e.g. lanthanum chloride) so that the pH of the resulting aqueous phase of the mixture is below 10.5; acidified calcined clays, such as metakaolin, spinel phase kaolin, calcined bentonite, calcined halloysite, and calcined attapulgite that have been contacted with one or more acidic solutions containing sulfuric acid, hydrochloric acid, nitric acid, or other acidic compounds (e.g. acetic acid) so that the pH of the resulting aqueous phase of the mixture is below 10.5; salts, such as aluminum sulfate, magnesium sulfate, calcium carbonate, and particularly deliquescent acidic salts, such as calcium chloride, magnesium chloride, lithium chloride, and magnesium nitrate; solid acids, such as boric acid, tartaric acid and citric acid; organic acid anhydrides such as phthalic anhydride, maleic anhydride, succinic anhydride and glutaric anhydride; and mixtures thereof.

A preferred Second Material is metakaolin microspheres. As used herein the term "microspheres" shall mean nominally spherical particles having an average particle size of from about 50 to 100 microns. Metakaolin microspheres are comprised substantially of metakaolin and may be prepared by the procedure described in the Preparation of Raw Materials section set forth below.

The following procedure may be utilized to ascertain whether a material is a suitable Second Material for forming a mixture with the metal chlorite for purposes of the present invention:

Dry Air: An intimate physical mixture of the desired amounts of the metal chlorite (e.g. sodium chlorite) and a proposed Second Material is prepared and stored under dry conditions. A one gram portion of the mixture is placed, at room temperature, into a dry, sealed one gallon polyethylene enclosure which is purged at a flow rate of about 10 cc/min with dry air (i.e. a dew point of no greater than −50° C.). The chlorine dioxide concentration of the gas within the enclosure is measured periodically over a period of about 72 hours. The Second Material has acceptable dry stability if the resultant chlorine dioxide gas concentration is less than about 0.025 ppm during this Dry Air test even if said Second Material exhibits an initial and brief release of chlorine dioxide gas which results in a concentration in excess of 0.025 ppm because of the presence of a small amount of residual water in the solids and/or the enclosure.

Humid Air: A second one gram portion of the mixture used in the Dry Air test step above is exposed to about 80% relative humidity air at room temperature in a sealed one gallon polyethylene enclosure which is purged at a flow rate of about 10 cc/min with 80% relative humidity air. The chlorine dioxide gas concentration within the enclosure is measured periodically over a period of about 7 days.

A material is considered an acceptable Second Material for use herein if it exhibits both acceptable stability in the Dry Air test above and if at any time during the Humid Air test above it yields a sustained concentration (defined hereinbelow) of chlorine dioxide gas equal to or in excess of about 0.025 ppm in a controlled release manner.

In accordance with the present invention, the mixture of the metal chlorite and the Second Material generates the chlorine dioxide gas in a sustained concentration of from about 0.025 to 1,000 ppm.

The measurement of chlorine dioxide gas is made in the atmosphere into which the chlorine dioxide gas is generated. For example, if the generating mixture is exposed to water vapor in air, the concentration of chlorine dioxide gas in ppm will be measured based on the total atmosphere including the air and water vapor.

As previously indicated, chlorine dioxide gas is produced in accordance with the present invention in a sustained concentration of from about 0.025 to 1,000 ppm. The phrase "sustained concentration" means that at all times during production, the concentration of chlorine dioxide gas is within the range 0.025 to 1,000 ppm. The generation of chlorine dioxide gas need not be at a constant rate. It is permissible to have a fluctuating rate so long as the chlorine dioxide gas concentration does not exceed 1,000 ppm, and is within the range of from about 0.025 to 1,000 ppm for a sustained period of time as hereinafter defined.

According to the invention, the generation of chlorine dioxide gas within the specified range will vary depending on the relative humidity of the surrounding atmosphere, the ratio of the reactants in the mixture, the diluent gas flow rate (e.g. air) through the treated space, and the ratio of the amount of chlorine dioxide gas releasing material to the volume of the treated space. Generally, the higher the relative humidity the higher the rate of production of chlorine dioxide gas. The lower the flow of the diluent gas through the treated space, the higher the resultant chlorine dioxide gas concentration. The higher the ratio of the chlorine dioxide gas releasing material to the volume of the treated space, the higher the chlorine dioxide gas concentration. In a preferred embodiment of the invention, the sustained amount of chlorine dioxide gas is from about 0.025 to 500 ppm, most preferably from about 0.025 to 100 ppm. Especially good results are obtained when the chlorine dioxide gas production is in the range of from about 0.025 to 50 ppm.

The amount of each of the metal chlorite and the Second Material will depend on several factors, including, but not limited to, the quantity of chlorine dioxide gas needed for a particular application, the basicity of the metal chlorite and the acidity of the Second Material. In general, it is preferred to use as much chlorite as possible consistent with a sufficient rate of release. As a consequence, the yield of chlorine dioxide per unit mass of the mixture is maximized. In general, the weight ratio of the metal chlorite and the Second Material is in the range of from about 0.001 to 0.25:1.0. It is within the skill of the art to choose the proper ratio for a particular application.

The mixture formed in accordance with the present invention may optionally contain at least one desiccant which absorbs water to minimize or eliminate an initial brief duration production of chlorine dioxide gas due to residual water vapor present in the atmosphere or in the solids when the mixture is packaged. Suitable desiccants include but are not limited to activated calcium chloride, activated calcium sulfate, activated zeolite X, activated zeolite A, activated bentonite clay, activated silica gel, activated attapulgite and mixtures thereof. The term "activated" means that the particular material has been substantially dehydrated, for example, by heating at 300° C. for about one hour. The total amount of desiccant may vary depending on several factors, for example, the ambient humidity when the material is packaged, the water permeability of the packaging material and the desired shelf life of the product. Generally, the desiccant is present in a total amount from about 0.1% to 25% by weight based on the total weight of the mixture.

In the practice of the present invention, the relative humidity of the atmosphere to which the composition is exposed during use can range from low to high humidity conditions. The method of the present invention can be conducted at low humidity (e.g. 10% relative humidity) up to 100% relative humidity. As previously indicated, the amount of chlorine dioxide gas generated per given amount of the mixture will depend, in part, on the relative humidity of the surrounding atmosphere. In general, higher humidity will result in a higher concentration of chlorine dioxide gas.

For example, it has been observed that the production of chlorine dioxide gas will approximately double when the relative humidity is increased from about 10% to about 80% at room temperature. It has also been observed that at ambient room temperature compared to 32° F., there is no significant change in the production rate of chlorine dioxide.

It will be understood that for a given unit of the mixture, a sustained amount of chlorine dioxide gas will be produced. For commercial applications, it may be desirable to employ multiple units of the mixture. In some cases it will be desirable to initiate the production of chlorine dioxide gas from one or more units of the mixture and then to have a second group or multiple groups of units of the mixture be added at a later time. Furthermore, one of the constituents of the composition of the present invention may be present in excess and the second of the constituents may be added as needed. For example, the composition can initially contain an excess of Second Material, as for example, acid treated metakaolin microspheres, and periodically additional amounts of metal chlorite can be added.

The mixture of the metal chlorite and the Second Material can be formulated in several ways. The preferred method is to prepare in a dry atmosphere an intimate physical mixture of fine powders of both constituents having particle sizes preferably below about 200 um. Larger particles may be used and may achieve a slower rate of chlorine dioxide gas release in certain instances.

The mixture can also be formed by combining one of the constituents in liquid form with other constituent(s). For example, a slurry of a fine powder of calcined kaolin microspheres in a nonpolar liquid such as dodecane may be combined with the metal chlorite. The mixture is then dried to remove the nonpolar liquid. If water is used as the liquid, then the mixture should be quickly dried to a sufficient extent to prevent excessive release of chlorine dioxide gas.

The reaction of the metal chlorite and the Second Material can last for a sustained period of time. The term "sustained period of time" shall mean that the chlorine dioxide gas will be generated during a short period of time (several minutes) to a long period of time spanning many hours. The length of the sustained period of time will depend, for example, on the relative amounts of the constituents in the mixture. Eventually, of course, one of the reacting constituents (either the metal chlorite or the Second Material) will be spent and the reaction will cease. However, during the course of the reaction for however long it lasts, chlorine dioxide gas will be produced in a sustained concentration as defined herein.

A preferred composition for producing a slow release rate of long duration is a mixture of about 5% sodium chlorite and about 95% metakaolin microspheres. A preferred composition for a shorter duration, higher rate of generation of chlorine dioxide is a mixture of about 5% sodium chlorite, about 10% activated calcium chloride and the balance acid-treated metakaolin microspheres.

The length of time of the reaction is also dependent, in part, on how much water vapor is present in the atmosphere contained within the packaging. The optional use of desiccants to minimize chlorine dioxide gas production in the packaging during storage can ensure that the mixture will react for the longest period of time when exposed to water vapor under operating conditions. However, the presence of a desiccant may delay the desired onset of production of the chlorine dioxide gas when the mixture is exposed to water vapor.

The present invention can be utilized for a variety of commercial applications involving solid, liquid and/or gaseous environments. For, example the chlorine dioxide gas can be used to treat solids such as those having metal, fabric, wood and/or plastic surfaces. The chlorine dioxide gas can also be used to treat animal waste, pet and livestock litters, medical devices including bandages, ostomy devices and medical instruments, food products including meats, vegetables, fruits, grains and nuts; as well as items made from fabrics including drapes, wall hangings, upholstery, and clothes. Examples of liquids which can be treated with chlorine dioxide gas include liquid waste and water including potable water. Examples of gaseous environments which may be treated include those containing noxious and/or objectionable gases such as animal environments, smoke-laden environments (e.g. tobacco smoke), and exhaust systems from noxious gas producing facilities (e.g. chemical plants).

The materials of this invention may also be used to help prevent the incorporation of unwanted substances (including possibly toxic substances) which may affect the taste and odor in ice produced by ice machines, particularly in large volume ice production such as in commercial applications. It is well known that after prolonged use, the ice producing chambers of such ice machines can accumulate microbes (including pathogenic microbes) and microbial films which may emit harmful or unpleasant smelling and tasting gaseous and other byproducts. Such byproducts can accumulate in or on the ice being produced either before, during or after the water freezing process. However, it is believed that, the taste and odor of the ice being produced will be less affected and will not deteriorate to a substantial degree when materials of the present invention are used to generate and maintain a concentration of chlorine dioxide gas from between about 0.01 to about 10.0 ppm and preferably from about 0.01 to about 1.0 ppm within the ice producing chamber of an ice machine. It is believed that the chlorine dioxide gas produced in accordance with the practice of this invention, destroys the unpleasant smelling and tasting microbial byproducts so that they do not contaminate the ice. At higher concentrations of chlorine dioxide gas, the microbes themselves may be destroyed by the chlorine dioxide gas.

The mixture of metal chlorite and a Second Material in the presence of water vapor may be packaged for shipment and storage in containers made of materials which are resistant to the passage of liquid water and water vapor. Examples of such materials include metal cans, glass jars, foil pouches, and barrier layer polymer laminates.

The mixture of the metal chlorite and the Second Material may be used as a powder, used as formed shapes, or packaged and retained for use in any material which is gas permeable. Preferably, any packaging material for retained use is substantially impervious to liquid water. Examples of such materials include TYVEK® and GORTEX®. These materials enable water vapor to enter into the package and react with the mixture and also enable the resulting chlorine dioxide gas to be released from the package and enter the atmosphere. Such materials are substantially liquid water impervious.

Test Procedure

Unless specified otherwise, the following test procedure was used to evaluate the samples prepared in the following examples. One gram of the specified material was placed as a thin layer into a 2 inch diameter crystallizing dish. The dish was placed into a one gallon resealable polyethylene bag that was fitted with gas entry and exit ports near opposite corners. The bag was purged and mildly pressurized to a pressure of about 0.1 inch water column through the gas entry fitting with dry air or air of the desired humidity. The bag was then continuously purged at a flow rate of about 10 cc/min with air. A back pressure of about 0.1 inch water column was maintained by venting the purge gas through a tube that was kept just below the surface of a water reservoir. The chlorine dioxide gas within the bag was analyzed by replacing the gas outlet vent tube with a gas sampling tube and withdrawing a sample through a gas analysis tube (Draeger® model CH24301).

Dry air was supplied by a laboratory compressed air system and further purified by passing it through a 13× molecular sieve trap (Hewlett Packard model GMT-4-HP). Air having about 80% relative humidity was prepared by bubbling laboratory compressed air at a rate of about 200 cc/min through a one liter beaker filled with about 500 cc of stirred, saturated ammonium sulfate solution at room temperature within a polyethylene glove bag having an internal volume of about 20 liters. An internal pressure of about ½ inch water column was maintained within the bag by venting a portion of the gas through a sidearm immersed about ½ inch into a column of water.

Preparative Examples

I. Technical grade flaked sodium chlorite, nominally 80% purity with the remaining 20% reported to be sodium chloride (available from Acros, Aldrich Chemical Co. and Alfa Aesar) was dried for 3 hours at 150° C., and cooled to room temperature in a sealed container.

II. Aqueous impregnation of sodium chlorite was performed using a saturated solution of sodium chlorite that was prepared by mixing excess granular sodium chlorite with deionized water for one hour at 35° C., cooling to room temperature, stirring overnight at room temperature, and then filtering the resultant solids containing solution to remove the solids and leave a clear, saturated solution.

III. Dry calcium chloride and potassium chloride were supplied as technical grade granular solids (supplied by TJ Baker Co. and Aldrich Chemical Co., respectively). Each was dried for 3 hours at 300° C. and then cooled in sealed containers prior to use.

IV. Metakaolin microspheres were prepared by spray drying an aqueous slurry of white hydrous Georgia kaolin clay having a solids content of about 28–44% and a particle size distribution of about 80% by weight finer than one um, and dispersed with up to 2% by weight of the clay of a 25% to 30% solution of sodium silicate having a molar ratio of $SiO_2:Na_2O$ of 2.0 to 3.3 using a wheel atomizing spray dryer to produce spherical kaolin agglomerates having an average particle size of about 70 um. The agglomerates were calcined in a commercial rotary calciner for a time and temperature sufficient to convert substantially all of the hydrous kaolin to metakaolin (e.g. one hour at 700° C.).

V. Microspheres of kaolin clay that were calcined through the characteristic kaolin exotherm were produced in a similar fashion to the metakaolin microspheres, except that the calcination temperature was higher (e.g. one hour at 1,000° C.). The hydrous kaolin clay underwent the characteristic exothermic transformation to the spinel phase precursor to mullite without the formation of a substantial quantity of mullite. The resulting material is called "spinel phase microspheres".

VI. Acid treated metakaolin microspheres were prepared by impregnating about 300 grams of metakaolin microspheres prepared as above with 280 grams of 2.16N sulfuric acid solution, drying at 100° C., and calcining at 350° C. for 3 hours.

Prior to incorporation into the mixtures of the present invention, the metakaolin microspheres and the spinel phase microspheres were heat treated at 300° C. for 3 hours in a lab oven and then cooled to room temperature in a sealed container.

The following examples are illustrative of embodiments of the invention and are not intended to limit the invention as encompassed by the claims forming part of the Application.

Example 1

First Mixture: 200 grams of metakaolin microspheres prepared as in Preparative Example IV were mixed with 12.5 grams of dried sodium chlorite prepared as in Preparative Example I with mild hand grinding with a mortar and pestle under ambient room air conditions. The mixed sample was placed in a sealed glass jar wrapped with opaque tape.

Second Mixture: 200 grams of metakaolin microspheres were mixed with 12.5 grams of dried sodium chlorite with mild hand grinding with a mortar and pestle under dry air conditions at a dew point below about −20° C. in a glove bag. The mixed sample was placed in a sealed glass jar wrapped with opaque tape.

One gram of the First Mixture was tested under dry conditions as described in the Test Procedure. The results are shown in FIG. 1. An initial trace (0.3 ppm) of chlorine dioxide gas was detected over the first five hours which was probably due to water initially present in the sample, but no further chlorine dioxide gas was detected through 195 hours. At that point the dry air stream was humidified to about 80% relative humidity. The concentration of chlorine dioxide gas increased to 1 ppm and remained at 1 ppm until the test was concluded at about 250 hours.

Another one gram sample of the First Mixture was tested under 80% relative humidity conditions as described in the Test Procedure. The results are also shown in FIG. 1. The concentration of chlorine dioxide gas increased from 0 to 2 ppm in 19 hours, and ranged between 1 and 2 ppm through about 360 hours of the test.

Figure 2:
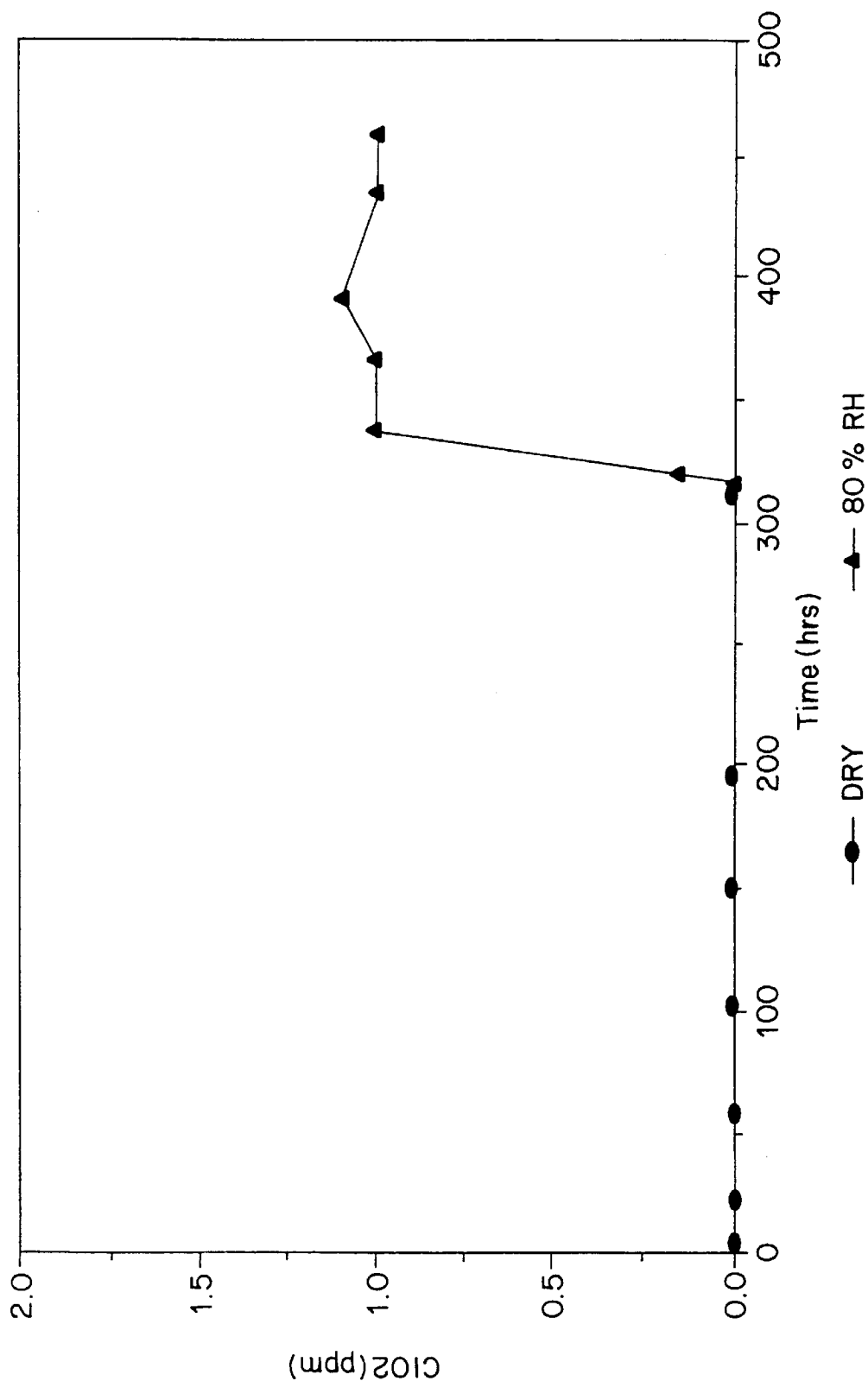
FIG. 2 is a graph showing the production of chlorine dioxide gas under dry and humid conditions for the second mixture prepared in accordance with Example 1.

One gram of the Second Mixture was tested under dry conditions as described in the Test Procedure. The results are shown in FIG. 2. No chlorine dioxide gas was detected over the 313 hours of testing under dry conditions. At that point the dry air stream was humidified to about 80% relative humidity. The concentration of chlorine dioxide gas increased to 1 ppm and stayed between 1 and 1.1 ppm. until the test was concluded at 450 hours.

The results shown in FIGS. 1 and 2 illustrate that the mixtures prepared in accordance with Example 1 have both stability under dry conditions and the ability to release chlorine dioxide gas upon exposure to humidity. Furthermore, they show that the trace initial release from the First Mixture was probably the result of water absorbed during sample preparation in ambient air, and, if desired, even that minor degree of premature release can be eliminated by preparing the material under dry conditions.

Example 2

A. 200 grams of spinel phase microspheres prepared as in Preparative Example V were mixed with 12.5 grams of dried sodium chlorite with mild hand grinding with a mortar and pestle under ambient room air conditions. The mixed sample was placed in a sealed glass jar wrapped with opaque tape.

B. One gram of the mixture prepared as in paragraph A above was tested at about 80% relative humidity. Chlorine dioxide gas was first detected after 5.5 hours. The concentration of chlorine dioxide gas peaked at 1 ppm after 94 hours, and the concentration of chlorine dioxide gas was 0.15 ppm after 364 hours.

Example 3

A. Acid activated bentonite clay was prepared as follows. A slurry was prepared containing Engelhard F100™ brand bentonite clay and oxalic acid (1 gm clay/10 ml of 2M oxalic acid solution). The slurry was heated to 90° C. for 6 hours, filtered, washed 3 times with deionized water, dried at 105° C., and then calcined for 3 hours at 350° C.

B. 50 grams of acid activated bentonite clay prepared as in paragraph A above was mixed with 3.2 grams of dried sodium chlorite with mild hand grinding with a mortar and pestle under dry air within a glove bag. The mixed sample was placed in a sealed glass jar wrapped with opaque tape.

C. The mixture prepared as in paragraph B above was tested as described in the Test Procedure. Under dry conditions no chlorine dioxide gas was detected after 72 hours of testing. Under humid conditions a trace (0.1 ppm) of chlorine dioxide gas was detected after 5 hours; the concentration peaked at 2.5 ppm after 45.5 hours, and was at 2.25 ppm after 72 hours when the test ended.

Example 4

A. Microspheres from an intermediate stage of the process of manufacturing a constituent of commercial fluid catalytic cracking catalyst comprising about 70% by weight of zeolite Y in its sodium ion exchanged form (NaY, Si/Al=2.58) and 30% of a noncrystalline sodium-silica-alumina residue of the zeolite crystallization reaction were dried for 3 hours at 450° C. (see for example, Example 4 in U.S. Pat. No. 5,395,809). When mixed at a concentration of about 30% by weight solids in water, the pH of the aqueous phase of the resultant slurry was about 8.

B. 200 grams of the dried NaY containing microspheres prepared as in paragraph A above was mixed with 12.5 grams of dried sodium chlorite with mild hand grinding with a mortar and pestle under ambient room conditions. The mixed sample was placed in a sealed glass jar wrapped with opaque tape.

C. The mixture prepared as in paragraph B above was tested as described in the Test Procedure. Under dry conditions no chlorine dioxide gas was detected during the first 196 hours of testing but chlorine dioxide gas (0.5 ppm) was detected after 313 hours and a lesser amount (0.1 ppm) was still present at 337 hours when the test ended. This result shows that the material has between about one and two weeks of shelf life, so it would be satisfactory for use in applications where there is only a slight delay between mixing and use.

When the mixture prepared as in paragraph B above was exposed to humid conditions, chlorine dioxide gas was first detected after 54 hours of exposure (2.6 ppm). The concentration remained from between about 1 and about 3 ppm through 364 hours when the test was ended.

Example 5

A. Sodium hydrogen zeolite Y (NaHY) powder was prepared as follows: 25 grams of sodium Y zeolite powder (Si/Al=2.34 Aldrich) was slurried in 250 ml of 5 weight percent ammonium sulfate solution. The aqueous phase of the resultant slurry had a pH of 6.5. The slurry was heated to 90° C. with stirring for 2 hours, and filtered to separate the solid zeolite from the solution. The solid was washed with about 200 grams of deionized water 5 times, and dried to a temperature of about 105° C. The dried solid was calcined for 2 hours at a temperature of 450° C. in a thin layer in an open tray, and cooled to room temperature in a sealed container.

B. Another material was prepared by impregnating 8 grams of NaHY powder prepared as in paragraph A above with 1.6 grams of a saturated solution of sodium chlorite. The impregnation was done by adding the solution to the powder dropwise with rapid stirring to maximize the rapid distribution of the solution through the powder. The mixture of sodium chlorite impregnated zeolite was not dried after the impregnation step. It was stored in a sealed glass container covered with opaque tape.

C. The mixture prepared as in paragraph B above was tested according to the Test Procedure. Under dry conditions chlorine dioxide gas was released at 2 hours and the concentration of chlorine dioxide gas remained between 3 and 4.5 ppm throughout the 26 hour test. Under humid conditions the mixture generated between 3 and 4.5 ppm of chlorine dioxide gas for the first 48 hours. The concentration of chlorine dioxide gas diminished slowly thereafter to zero after 150 hours of exposure to the humid atmosphere.

Example 6

A. 10 grams of dried calcium chloride prepared as in Preparative Example III was mixed with 0.75 grams of dried sodium chlorite with mild hand grinding with a mortar and pestle under ambient room air conditions. The mixed sample was placed in a sealed glass jar wrapped with opaque tape.

B. The mixture prepared as in paragraph A above was tested according to the Test Procedure. Under dry conditions no chlorine dioxide gas was detected over 72 hours of testing. Under humid conditions there was no chlorine dioxide gas detected through 54 hours, an amount (0.25 ppm) was detected at 94 hours, and the generation of chlorine dioxide gas remained steady at a concentration of between about 1 and 2 ppm for 364 hours.

Example 7

A. 84 grams of acid treated metakaolin microspheres prepared as in Preparative Example VI was mixed with 10 grams of dried calcium chloride with mild hand grinding with a mortar and pestle under ambient room air conditions. The resultant mixture was dried for 2 hours at 200° C. and cooled to room temperature in a sealed glass jar wrapped with opaque tape.

B. The mixture prepared as in paragraph A above was combined with 5.25 grams of dried sodium chlorite with mild hand grinding with a mortar and pestle under ambient room air conditions. The mixed sample was placed in a sealed glass jar wrapped with opaque tape.

C. The mixture prepared as in paragraph B above was tested according to the Test Procedure. Under dry conditions no chlorine dioxide gas was detected over 72 hours of testing. Under humid conditions a trace (0.05 ppm ) of chlorine dioxide gas was detected after 4 hours. The chlorine dioxide gas concentration peaked at 6.25 ppm after 26 hours, and fell to zero after 172 hours.

Example 8

A. A material was prepared as follows. 10 grams of stearic acid (Aldrich) was mixed with 0.75 grams of dried sodium chlorite with mild hand grinding with a mortar and pestle under ambient room air conditions. The mixed sample was placed in a sealed glass jar wrapped with opaque tape.

B. The mixture prepared as in paragraph A above was tested at 80% relative humidity according to the Test Procedure. No chlorine dioxide gas was detected over 8 days of testing.

Example 9

A. A mixture in accordance with the present invention was prepared as follows. Commercial 13× zeolite powder (Aldrich) was dried for 3 hours at 300° C. and cooled to room temperature in a sealed container. When slurried at 30 weight percent solids in water, the aqueous phase of the slurry had a pH of 9.7. 10 grams of dried 13× powder was mixed with 0.8 grams of dried sodium chlorite with mild hand grinding with a mortar and pestle under ambient room air conditions. The mixture was stored in a sealed glass container covered with opaque tape.

B. The mixture prepared as in paragraph A above was tested according to the Test Procedure. Under dry conditions no chlorine dioxide gas was detected over 144 hours of testing. Under humid conditions a trace (0.05 ppm) of chlorine dioxide gas was detected after 96 hours. The chlorine dioxide gas concentration varied between 0.025 and 0.05 ppm through the remainder of the 168 hour test.

Example 10

A. 50 grams of acid treated metakaolin microspheres was mixed with 5 grams of dried potassium chloride prepared as in Preparative Example III with mild grinding with a mortar and pestle under ambient room air conditions. The resultant mixture was dried for 2 hours at 200° C. and cooled to room temperature in a sealed container.

B. The mixture prepared as in paragraph A above was combined with 3.125 grams of dried sodium chlorite with mild hand grinding with a mortar and pestle under ambient room air conditions. The resulting mixture was placed in a sealed glass jar wrapped with opaque tape.

C. The mixture prepared as in paragraph B above was tested in humid air according to the Test Procedure. A trace (0.1 ppm) of chlorine dioxide gas was detected after 45 minutes, and the chlorine dioxide gas concentration ranged between about 1 and 3 ppm between about 4 and 290 hours when the test was ended.

Example 11

Microspheres comprising 80% zeolite X (having a $SiO_2$ to $Al_2O_3$ ratio equal to one) in its mixed sodium and potassium ion exchanged forms and 20% of the crystallization residue of calcined kaolin clay were produced by reacting metakaolin microspheres in an aqueous solution of sodium hydroxide, potassium hydroxide, and sodium silicate at 75° C. The solids were filtered and washed with deionized water until the effluent pH was about 10.5. The solids were then dried for 3 hours at 300° C. and cooled to room temperature in a sealed container. When slurried at 30 weight percent solids in water, the aqueous phase of the slurry had a pH of 10.3. 12 grams of the dried microspheres were mixed with 0.8 grams of dried sodium chlorite with mild hand grinding with a mortar and pestle under ambient room air conditions. The mixture was stored in a sealed glass container covered with opaque tape.

The mixture was tested according to the Test Procedure. Under dry conditions no chlorine dioxide gas was detected over 144 hours of testing. Under humid conditions a trace (0.1 ppm) of chlorine dioxide gas was detected after 46 hours. The release of chlorine dioxide gas increased slowly to a peak of 0.5 ppm at 124 hours, and was at 0.4 ppm after 143 hours when the test was ended.

Example 12

Three samples, each in the form of a powder prepared in an accordance with Examples 1, 4 and 7, respectively, were tested to determine the storage stability of the composition of the present invention by the following procedure.

Individual one gram samples were stored in sealed glass jars. Chemical analysis of each of the samples was performed by extracting the water soluble constituents into a pH 7 buffered aqueous solution at room temperature. The respective solutions were analyzed for chlorate, chlorite and chloride anion concentration using ion chromatography following the general procedures of EPA test method 300. The chlorite analytical standard was prepared from technical grade solid sodium chlorite which was assumed to comprise about 80% by weight of pure sodium chlorite. The results are shown in FIG. 3.

Figure 3:
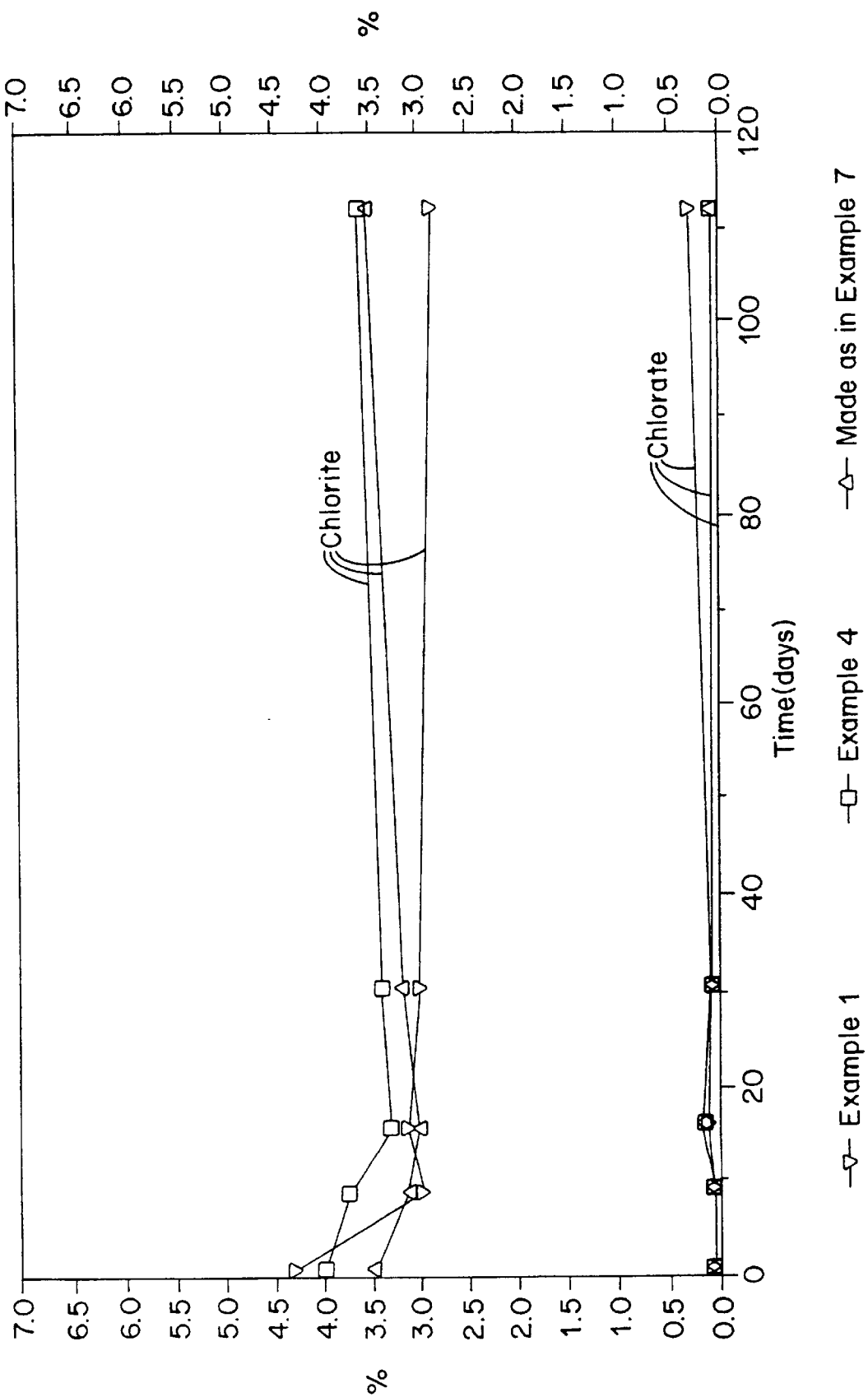
FIG. 3 is a graph showing the concentrations of chlorite and chlorate anions in powdered samples during storage under dry conditions for several mixtures prepared in accordance with the present invention.

As shown in FIG. 3, except for a small initial decrease in chlorite concentration, the chlorite and chlorate concentrations of each sample were unchanged for a period of 112 days of storage, indicating that the samples possessed excellent storage stability.

What is claimed is:

1. A method for producing ice having substantially no undesirable taste and odor characteristics which comprises freezing water in the presence of chlorine dioxide gas.

2. The method of claim 1 wherein the chlorine dioxide gas is present in a concentration from about 0.01 ppm to about 10.0 ppm.

3. The method of claim 1 wherein the chlorine dioxide gas is present in a concentration from about 0.01 ppm to about 1.0 ppm.

4. A method for obtaining ice having substantially no undesirable taste and odor characteristics which comprises contacting said ice with chlorine dioxide gas.

5. The method of claim 4 wherein the chlorine dioxide gas is present in a concentration from about 0.01 ppm to about 10.0 ppm.

6. The method of claim 4 wherein the chlorine dioxide gas is present in a concentration from about 0.01 ppm to about 1.0 ppm.

7. A method for producing ice having substantially no undesirable taste and odor characteristics by freezing water in an ice machine, which method comprises maintaining a concentration of chlorine dioxide gas in the ice producing chamber of said ice machine before, during or after the freezing process.

8. The method of claim 7 wherein the chlorine dioxide gas is present in a concentration from about 0.01 ppm to about 10.0 ppm.

9. The method of claim 7 wherein the chlorine dioxide gas is present in a concentration from about 0.01 ppm to about 1.0 ppm.

* * * * *